US00PP37304P2

(12) United States Plant Patent
Schoone

(10) Patent No.: US PP37,304 P2
(45) Date of Patent: Mar. 3, 2026

(54) ***PHALAENOPSIS* PLANT NAMED 'Florichrome'**

(50) Latin Name: *Phalaenopsis hybrida*
Varietal Denomination: Florichrome

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 19/310,827

(22) Filed: Aug. 26, 2025

Related U.S. Application Data

(60) Provisional application No. 63/690,656, filed on Sep. 4, 2024.

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Phalaenopsis* plant named 'Florichrome', characterized by its upright plant habit; moderately vigorous to vigorous growth habit; strong flowering stems; healthy and sturdy leaves; freely flowering habit with typically two inflorescences developing per plant, each inflorescence with numerous flowers; flower petals and sepals that are purplish red in color with pale yellow-colored narrow marginal edges and distinct venation; and good postproduction longevity.

2 Drawing Sheets

CROSS-REFERENCED TO CLOSELY-RELATED APPLICATIONS

Figure 1:
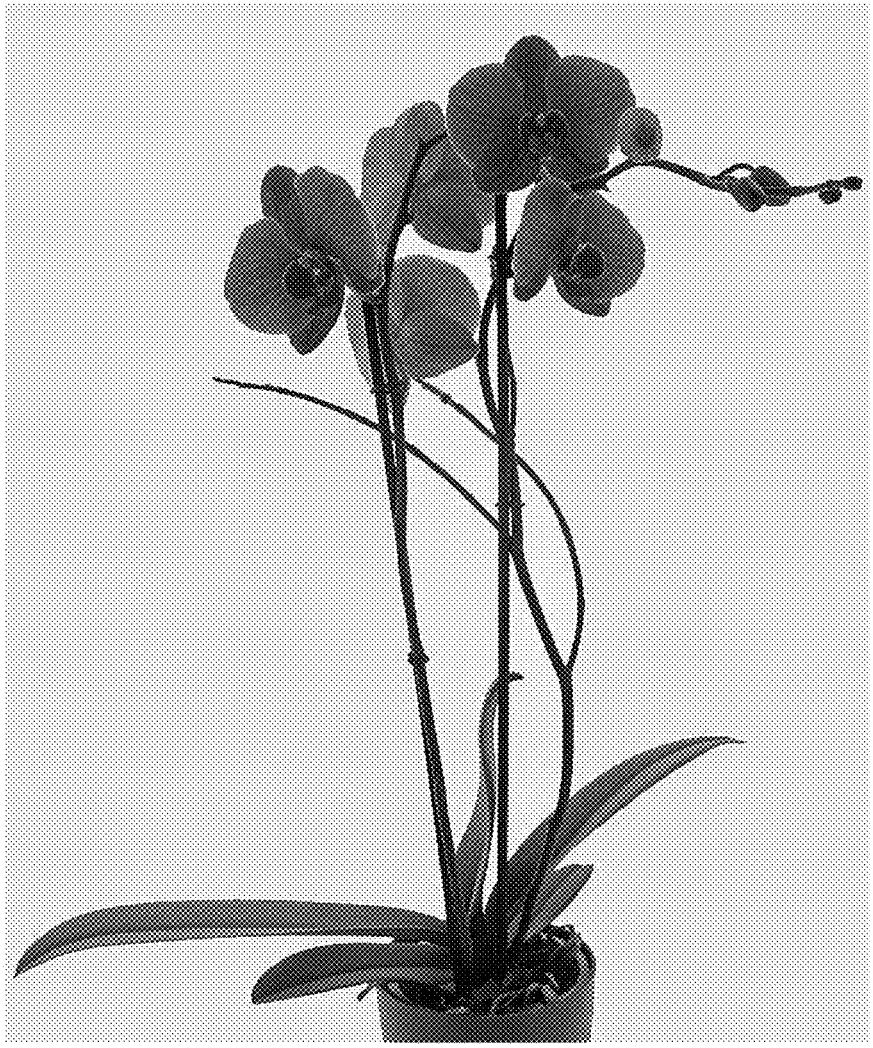

Title: Varieties of *Phalaenopsis* Plants
Inventor: René Schoone
Filed: Sep. 4, 2024
Ser. No. 63/690,656
Inventor and Applicant/Assignee hereby claims the benefit of this provisional U.S. Patent Application.

A European Community Plant Breeder's Rights application for the instant plant was filed by the Applicant/Assignee, Floricultura B.V. of Heemskerk, The Netherlands on Oct. 9, 2024, application number 2024/2357. Foreign priority is not claimed to this application.

Botanical designation: *Phalaenopsis hybrida.*
Cultivar denomination: 'FLORICHROME'.

BACKGROUND OF THE INVENTION

The present invention relates to a new and distinct cultivar of *Phalaenopsis* plant, botanically known as *Phalaenopsis hybrida*, and hereinafter referred to by the name 'Florichrome'.

The new *Phalaenopsis* plant is a product of a planned breeding program conducted by the Inventor in Assendelft and Heemskerk, The Netherlands. The objective of the breeding program is to develop new fast-growing and freely flowering *Phalaenopsis* plants with good leaf shape and flowers with unique coloration and color patterns.

The new *Phalaenopsis* plant originated from a cross-pollination in May 2014 in Assendelft, The Netherlands of a proprietary breeding selection of *Phalaenopsis hybrida* identified as code number JM123, not patented, as the female, or seed, parent with a proprietary selection of *Phalaenopsis hybrida* identified as code number JM815, not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in October 2020.

Asexual reproduction of the new *Phalaenopsis* plant by in vitro meristem propagation in a controlled environment in Assendelft, The Netherlands since October 2021 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Florichrome'. These characteristics in combination distinguish 'Florichrome' as a new and distinct *Phalaenopsis* plant:

1. Upright plant habit.
2. Moderately vigorous to vigorous growth habit.
3. Strong flowering stems.
4. Healthy and sturdy leaves.
5. Freely flowering habit with typically two inflorescences developing per plant, each inflorescence with numerous flowers.

6. Flower petals and sepals that are purplish red in color with pale yellow-colored narrow marginal edges and distinct venation.
7. Good postproduction longevity.

Plants of the new *Phalaenopsis* can be compared to plants of the female parent selection. Plants of the new *Phalaenopsis* differ primarily from plants of the female parent selection in the following characteristics:

1. Flower petals and sepals of plants of the new *Phalaenopsis* are purplish red in color with pale yellow-colored narrow marginal edges and distinct venation whereas flower petals and sepals of plants of the female parent selection are pink in color.
2. Flower petals and sepals of plants of the new *Phalaenopsis* have more distinct venation than flower petals and sepals of plants of the female parent selection.
3. Flower petals of plants of the new *Phalaenopsis* are not imbricate whereas flower petals of the female parent selection are imbricate.

Plants of the new *Phalaenopsis* can be compared to plants of the male parent selection. Plants of the new *Phalaenopsis* differ primarily from plants of the male parent selection in the following characteristics:

1. Flower petals and sepals of plants of the new *Phalaenopsis* are purplish red in color with pale yellow-colored narrow marginal edges and distinct venation whereas flower petals and sepals of plants of the male parent selection are purple in color.
2. Flower petals and sepals of plants of the new *Phalaenopsis* have distinct venation whereas flower petals and sepals of plants of the male parent selection do not have distinct venation.

Plants of the new *Phalaenopsis* can be compared to plants of x *Phalaenopsis hybrida* 'Narbonne', not patented. In side-by-side comparisons, plants of the new *Phalaenopsis* differ primarily from plants of 'Narbonne' in the following characteristics:

1. Flowers of plants of the new *Phalaenopsis* are broader than flowers of plants of 'Narbonne'.
2. Flower petals and sepals of plants of the new *Phalaenopsis* have more distinct venation than flower petals and sepals of plants of 'Narbonne'.
3. The lateral lobes of the flower labella of plants of the new *Phalaenopsis* are more inwardly curved than the lateral lobes of the flower labella of plants of 'Narbonne'.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'Florichrome' grown in a container.

Figure 2:
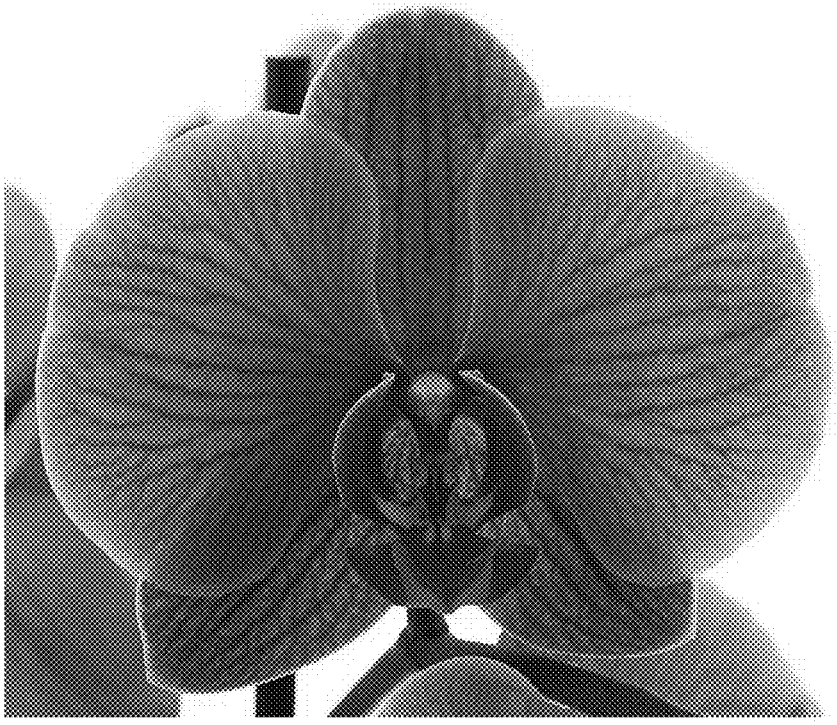

The photograph on the second sheet (FIG. 2) is a close-up view of a typical flower of 'Florichrome'.

DETAILED BOTANICAL DESCRIPTION

The aforementioned photographs and following observations and measurements describe plants grown during the winter in 11-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27° C. During the final months of production of the plants, day temperatures ranged from 20° C. to 22° C. and night temperatures ranged from 18° C. to 20° C. During the production of the plants, light levels ranged from a minimum of 5 klux to a maximum of 10 klux. In the following description, color references are made to The Royal Horticultural Society Colour Chart, 2015 Edition, except where general terms of ordinary dictionary significance are used.

Botanical classification: *Phalaenopsis hybrida* 'Florichrome'.

Parentage:

*Female, or seed, parent*.—Proprietary selection of *Phalaenopsis hybrida* identified as code number JM123, not patented.

*Male, or pollen, parent*.—Proprietary selection of *Phalaenopsis hybrida* identified as code number JM815, not patented.

Propagation:

*Type*.—By in vitro meristem propagation.

*Time to initiate roots, summer and winter*.—About two weeks at temperatures about 28° C. to 30° C.

*Time to produce a rooted young plant, summer and winter*.—About 20 to 25 weeks at temperatures about 28° C. to 30° C.

*Root description*.—Thin, fibrous; typically light yellowish white in color; actual color of the roots is dependent on substrate composition, water quality, fertilizer, substrate temperature and age of roots.

*Rooting habit*.—Freely branching; medium density.

Plant description:

*Plant form and growth habit*.—Herbaceous epiphyte; upright plant habit with typically two inflorescences developing per plant, each inflorescence with numerous flowers; monopodial; moderately vigorous to vigorous growth habit and moderate growth rate.

*Plant height, substrate level to top of foliar plane*.—About 18.7 cm.

*Plant height, substrate level to top of floral plane*.—About 48.1 cm.

*Plant diameter or spread*.—About 43.1 cm.

Leaf description:

*Arrangement and quantity*.—Distichous, simple; sessile; about four to five fully-developed leaves per plant.

*Length*.—About 23.8 cm.

*Width*.—About 7.4 cm.

*Aspect*.—Horizontal to outwardly arching.

*Shape*.—Narrowly obovate-oblong to obovate-oblong; slightly carinate.

*Apex*.—Unequal narrowly obtuse.

*Base*.—Sheathing. Sheath length: About 1.9 cm. Sheath width: About 1.6 cm. Sheath color, upper and lower surfaces: Close to 146A slightly to strongly tinged with close to N186C.

*Margin*.—Entire.

*Texture and luster, upper surface*.—Smooth, glabrous; semi-glossy.

*Texture and luster, lower surface*.—Smooth, glabrous; glossy.

*Venation pattern*.—Camptodromous.

*Color*.—Developing leaves, upper surface: Close to NN137B with narrow marginal edges, close to N186C. Developing leaves, lower surface: Close to 147B strongly tinged with close to N186C. Fully expanded leaves, upper surface: Close to a blend of 137B and 146A; venation, close to 147A; color becoming closer to a blend of N186C and 200B with subsequent development. Fully expanded leaves, lower surface: Close to a blend of 146A and 148A; at the margins, slightly tinged with close to N186B; venation, close to N186B.

Inflorescence description:

*Appearance and flowering habit*.—Showy zygomorphic flowers arranged on axillary simple or branched racemes; typically two inflorescences develop per plant; each inflorescence with about 14 flowers; flowers face mostly outwardly on outwardly arching inflorescences supported by upright peduncles; flowers with three petals, two lateral petals and one center petal transformed into a labellum and three sepals.

*Fragrance*.—None detected.

*Time to flower*.—Plants begin flowering about six months after planting; plants flower naturally during the winter into the spring.

*Flower longevity and postproduction longevity*.—Long flowering period and good postproduction longevity, individual flowers maintain good substance for about 14 weeks on the plant; flowers not persistent.

*Inflorescence length* (*lowermost flower to inflorescence apex*).—About 36.3 cm.

*Inflorescence width*.—About 17.5 cm.

*Flower buds* (*about one week before flower opening*).—Height: About 2 cm. Diameter: About 1.3 cm by 1.6 cm. Shape: Broadly ovoid. Color: Close to 152A; main veins, close to 178A.

*Flower size*.—About 8.6 cm (vertical) by 9.5 cm (horizontal).

*Flower depth*.—About 3.3 cm.

*Petals, quantity and arrangement*.—Three, two lateral petals and one center petal transformed into a labellum.

*Lateral petals*.—Length: About 4.6 cm. Width: About 6.2 cm. Shape: Broadly reniform; not imbricate. Apex: Obtuse. Margin: Entire. Texture and luster, upper and lower surfaces: Smooth, glabrous; velvety; matte. Color: When opening, upper surface: Close to 60C; towards the apex and margins, close to 59D and 63B; at the base, close to 61A; venation, close to 61A. When opening, lower surface: Close to 160A; towards the apex and margins, close to 180D; venation, close to 181B. Fully opened, upper surface: Close to 59D; towards the apex and margins, close to 64C; narrow marginal edges, close to 161D; at the base, close to 71B; venation, close to 71B; colors do not change with subsequent development. Fully opened, lower surface: Close to a blend of 69A, 161D and 182D; narrow marginal edges, close to 161D; venation, close to 75A; colors do not change with subsequent development.

*Labella*.—Appearance: Three-parted with two lateral lobes and a central lobe. Length, lateral lobes: About 2.3 cm. Width, lateral lobes: About 1.2 cm. Length, central lobe: About 2.4 cm. Width, central lobe: About 0.8 cm to 2.4 cm. Length, cirrhose apices: About 1.5 cm. Shape, lateral lobes: Obovate. Shape, central lobe: Rhomboidal with an elongated apex. Apex, lateral lobes: Obtuse. Apex, central lobe: Cleft with two cirrhose apices curled upwards and backwards. Margins, lateral and central lobes: Entire. Texture and luster, lateral and central lobes, upper and lower surfaces: Smooth, glabrous, velvety; matte. Callosities: Located at the base of the labellum and attachment point of the lateral petals; about 5 mm in length, about 6 mm in width and about 6 mm in height. Color, lateral lobes: When opening and fully opened, upper surface: Close to a blend of 187C and 187D; towards the apex, close to 70A; apical narrow marginal edges, close to 76D; at the base, axial stripes, close to 155A. When opening and fully opened, lower surface: Close to a blend of 187C and 187D; towards the apex, close to 70A and 70B; at the base, close to 158A. Color, central lobe: When opening, upper surface: Close to 187D; at the base, close to 161D with two small blotches, close to 10A and radial stripes, close to 187D; main vein, close to 187B; cirrhose apices, close to 187D with apices, close to N155B. When opening, lower surface: Close to a blend of 187C and 187D; towards the apex, close to N79C; central band, close to 182C; at the base, close to 160D; cirrhose apices, close to N79C with apices, close to N155B. Fully opened, upper surface: Close to 187D; towards the apex, slightly tinged with close to 10A; at the base, close to 161D with two small blotches, close to 10A and radial stripes, close to 187D; main vein, close to 187B; cirrhose apices, close to 187D with apices, close to N155B. Fully opened, lower surface: Close to a blend of 187C and 187D; towards the apex, close to N79C; central band, close to 182C; at the base, close to 160D; cirrhose apices, close to N79C with apices, close to N155B. Color, callosities: When developing: Close to 11C; towards the apex, close to 12B; fine dots and blotches, close to 181B. Fully developed: Close to 12C; towards the apex, close to 12B; fine dots and blotches, close to 181A.

*Sepals*.—Quantity and arrangement: Three, one upper dorsal sepal and two lower lateral sepals. Length, dorsal sepal: About 4.9 cm. Width, dorsal sepal: About 3.4 cm. Length, lateral sepals: About 4.8 cm. Width, lateral sepals: About 3.1 cm. Shape, dorsal sepal: Broadly elliptic-obovate. Shape, lateral sepals: Ovate. Apex, dorsal sepal: Minutely retuse. Apex, lateral sepals: Bluntly acute. Base, dorsal and lateral sepals: Cuneate. Margins, dorsal and lateral sepals: Entire. Texture and luster, dorsal and lateral sepals, upper and lower surfaces: Smooth, glabrous; moderately velvety; matte. Color, dorsal sepal: When opening, upper surface: Close to 59C; towards the base, close to 71A; narrow marginal edges, close to 158A and 158B; venation, close to 187D. When opening, lower surface: Close to 153D; towards the apex, tinged with close to 182C; venation, close to 182B. Fully opened, upper surface: Close to a blend of 63A and 184D; towards the base, close to 72A; narrow marginal edges, close to 158B; venation, close to 71A. Fully opened, lower surface: Close to 161D; towards the apex and margins, tinged with close to 182D; narrow marginal edges, close to 158B; venation, close to 182C. Color, lateral sepals:

When opening, upper surface: Close to 184C; towards the base, close to 160A and 160B; narrow marginal edges, close to 158A and 158B; venation, close to 187C and 187D. When opening, lower surface: Close to 153D; towards the apex, close to 183D; narrow marginal edges, close to 158A and 158B; venation, close to 175A. Fully opened, upper surface: Close to 184D; towards the base, close to 4D; narrow marginal edges, close to 158B; venation, close to a blend of 61A and 187D. Fully opened, lower surface: Close to 161C; towards the apex, close to 182D; narrow marginal edges, close to 158B; venation, close to 181B.

*Peduncles*.—Length: About 62.6 cm. Diameter: About 6 mm. Strength: Strong. Aspect: Upright to outwardly arching. Texture and luster: Smooth, glabrous; matte. Color: Close to N200A moderately covered with fine dots, close to 146D.

*Pedicels*.—Length: About 4 cm. Diameter: About 3 mm. Strength: Moderately strong. Aspect: About 50° from peduncle axis. Texture and luster: Smooth, glabrous; matte. Color: Close to 195A; distal end, close to 75C; proximal end, close to 200B.

*Reproductive organs*.—Androecium: Column length: About 9 mm. Column width: About 6 mm. Column color: Close to N78B. Pollinia quantity: Two. Pollinia diameter (per two pollinia): About 2 mm. Pollinia color: Close to 23A. Gynoecium: Stigma length: About 4 mm. Stigma width: About 4 mm. Stigma shape: Reniform. Stigma color: Close to N155A. Ovary length: About 1.3 cm. Ovary diameter: About 1 mm. Ovary color: Close to 150C. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'Florichrome' as herein illustrated and described.

* * * * *